(12) United States Patent
Lunsford

(10) Patent No.: US 10,166,898 B2
(45) Date of Patent: Jan. 1, 2019

(54) TRAVELER'S PERSONAL ARM REST DEVICE

(71) Applicant: Theodore Lunsford, Lakewood, CA (US)

(72) Inventor: Theodore Lunsford, Lakewood, CA (US)

( * ) Notice: Subject to any disclaimer, the term of this patent is extended or adjusted under 35 U.S.C. 154(b) by 172 days.

(21) Appl. No.: 15/157,245

(22) Filed: May 17, 2016

(65) Prior Publication Data
US 2017/0332795 A1 Nov. 23, 2017

(51) Int. Cl.
| | |
|---|---|
| *A61F 5/37* | (2006.01) |
| *B60N 2/75* | (2018.01) |
| *B64D 11/06* | (2006.01) |
| *A61F 5/01* | (2006.01) |
| *A61F 13/10* | (2006.01) |
| *A41D 13/08* | (2006.01) |

(52) U.S. Cl.
CPC .............. *B60N 2/75* (2018.02); *A61F 5/0118* (2013.01); *A61F 5/3723* (2013.01); *A61F 13/10* (2013.01); *B64D 11/06* (2013.01); *A41D 13/08* (2013.01); *A41D 2400/48* (2013.01)

(58) Field of Classification Search
CPC ..... A41D 13/081; A41D 13/08; A61F 5/3746; A45F 4/02
USPC .................................................. 297/411.21
See application file for complete search history.

(56) References Cited

U.S. PATENT DOCUMENTS

| | | | | |
|---|---|---|---|---|
| 1,266,688 | A * | 5/1918 | Kassner | A61F 5/3738 602/4 |
| 1,621,323 | A * | 3/1927 | Horn | A61F 5/3746 2/92 |
| 4,071,022 | A * | 1/1978 | Ewers | A61F 5/3738 602/4 |
| 4,526,164 | A * | 7/1985 | Bihl | A61F 5/3738 602/4 |
| 4,878,490 | A * | 11/1989 | Scott | A61F 5/3746 602/20 |
| 8,197,429 | B2 * | 6/2012 | Neseem | A61F 5/00 602/4 |
| 8,523,028 | B1 * | 9/2013 | Young | A47D 13/025 224/158 |
| 2008/0301847 | A1 * | 12/2008 | Holland | A41D 1/215 2/52 |

\* cited by examiner

*Primary Examiner* — Sarah B McPartlin
(74) *Attorney, Agent, or Firm* — Omni Legal Group; Omid E Khalifeh

(57) ABSTRACT

A traveler's personal arm rest device comprises a chest portion and a pair of shoulder straps configured to supportively maintain the chest portion against the anterior side of a wearer's torso. In an embodiment, the chest portion may be securely folded to define a tubular cavity sized to accommodate all of the wearer's arms therein so that such arms may be maintained and comfortably supported by way of the straps in a resting position that is in line with his or her own body. The disclosure may provide a wearer with increased comfort while seated in cramped modes of public transportation and further prevent passive aggressive and even assertive arguments with neighbors regarding available arm resting spaces. Elements enabling compact self-stowage when not in use, providing ergonomic support when worn, and permitting storage of personal belongings therein are also provided.

7 Claims, 3 Drawing Sheets

TRAVELER'S PERSONAL ARM REST DEVICE

GOVERNMENT CONTRACT

Not applicable.

CROSS-REFERENCE TO RELATED APPLICATIONS

Not applicable.

STATEMENT RE. FEDERALLY SPONSORED RESEARCH/DEVELOPMENT

Not applicable.

COPYRIGHT & TRADEMARK NOTICES

A portion of the disclosure of this patent document may contain material which is subject to copyright protection. This patent document may show and/or describe matter which is or may become trade dress of the owner. The copyright and trade dress owner has no objection to the facsimile reproduction by any one of the patent document or the patent disclosure, as it appears in the Patent and Trademark Office patent files or records, but otherwise reserves all copyrights and trade dress rights whatsoever.

TECHNICAL FIELD

The disclosed subject matter relates generally to traveler's accessories and garments and, more particularly, to a device configured to provide a traveler with a personal arm rest that avoids undesirably encroaching on strangers' spaces in cramped modes of public transportation.

BACKGROUND

Although long-distance travel via public modes of transportation—such as airplanes—has in recent years become less expensive and thus more accessible to the general public, certain concessions have had to be made. For instance, in order to accommodate greater numbers of passengers, seating spaces have notoriously become narrower, granting each traveler less and less personal space. A common complaint from travelers in such conditions is that neighboring passengers disrespect what is left of any personal space by overtaking shared portions defined by the seating arrangements. For example, "elbow wars" colloquially refers to passive aggressive and sometimes assertive disagreements over use of shared armrests.

Some solutions for clearly dividing shared spaces have been proposed. For instance, U.S. Pub. No. 2015/0084393 filed by Chang et al. teaches a portable arm rest divider which expands the surface area of the arm rest and provides a barrier that separates the space allotted to seated neighbors. As another example, U.S. Pat. No. 7,959,231 to Lee discloses an armrest defined by vertically separated planes which are designed to accommodate one each of neighboring travelers' forearms. Unfortunately, these still require each neighbor to tacitly accept the other into a portion of his shared space.

Some wearable devices have also been proposed to avoid the need for such compromise by placing an auxiliary arm support within the personal space defined by the traveler's own body. For instance, U.S. Pat. No. 6,973,691 to Cordova et al. discloses an elongated pillow support with a horizontal pocket for receiving arms therethrough; U.S. Pat. No. 6,966,069 to Booth teaches a traveler's blanket with integrated arm pockets; and U.S. Pat. No. 6,435,185 to Schimpl teaches an arm support formed as a sweater that rigidly maintains bent arms within a horizontal envelope formed in the body of the support.

Still, these proposed solutions are deficient for various reasons, including for example that they lack ergonomic support, storage capability, and adjustability, and the problem of comfortably resting arms over the course of travel persists. Thus, there remains a need for a personal, wearable armrest.

SUMMARY

The present disclosure is directed to a personal arm rest device which, briefly, comprises a chest portion folded to supportively accommodate a wearer's arms and a pair of shoulder straps configured to supportively maintain the chest portion against the anterior side of the wearer's torso.

For purposes of summarizing, certain aspects, advantages, and novel features have been described. It is to be understood that not all such advantages may be achieved in accordance with any one particular embodiment. Thus, the disclosed subject matter may be embodied or carried out in a manner that achieves or optimizes one advantage or group of advantages without achieving all advantages as may be taught or suggested.

In accordance with one embodiment, the device may comprise a chest portion configured to define a tubular cavity sized to accommodate one or both of the wearer's arms therein, as desired. For example, the chest portion may comprise an outside, an inside, a top end and a bottom end. Then, to form the tubular cavity, the bottom end may be secured along the inside of the chest portion. The bottom end may be fixedly secured such as by permanently threadedly stitching the bottom end along the inside of the chest portion, however, it is contemplated that the bottom end may alternatively be adjustably securable along the inside of the chest portion. For example, opposing hook and loop fasteners may be respectively secured to the inside of the chest portion and the bottom end so that the bottom end may be releasably and/or adjustably meshed with the inside of the chest portion. As another example, opposing male and female snapping members may be disposed along the inside of the chest portion and the bottom end so that the bottom end may be releasably mated along the inside of the chest portion.

In any event, it is contemplated that the chest portion may be configured to lay in a position corresponding to the anterior side of a wearer's torso so that the tubular cavity may maintain the wearer's arms in front of his body. To further maintain the chest portion—and wearer's arms—in this position, a first supportive strap and a second supportive strap may be horizontally spaced from one another, secured to the top end of the chest portion and outside bottom-most portion of tubular cavity defined by the chest portion, and configured to receive one each of a wearer's arms therethrough. Such supportive straps may thus be formed to respectively encircle at least a portion of the wearer's left-lateral and right-lateral torso, including his or her shoulders, so that the supportive straps may forcibly hold the chest portion against the wearer's chest.

In some embodiments, the supportive straps may be adjustable to comfortably fit wearers of various sizes. For example, one skilled in the art will recognize that each supportive strap may comprise a plastic or metal strap adjuster configured to slidably receive portions of the supportive strap threaded therethrough. Using such adjusters, the lengths of each of the first and second supportive straps may be increased or decreased as desired.

Other features may be provided to enhance a wearer's comfort as well. For instance, a first horizontal strap may be secured along the first supportive strap and a second horizontal strap may be secured along the second supportive strap. When worn by a traveler, the first and second horizontal straps may be secured to one another behind the wearer to prevent the supportive straps from slipping off the wearer's arms. One skilled in the art will recognize that this may also prevent the wearer from rounding his or her shoulders forward, toward his or her resting arms, in a slouched position. Such horizontal straps may be adjustable along the length of the supportive straps and also adjustable in terms of their own length to accommodate wearers of varied height and girth.

In some embodiments, at least a portion of the first and second supportive straps comprises padded material to comfortably absorb and disperse downward pressure from a wearer's resting arms upon his shoulders and/or neck. Likewise, at least a portion of the chest portion may comprise padded material to comfortably absorb and disperse inward pressure of the wearer's arms held against his or her chest.

The top end of the chest portion may define a concave space between the first and second supportive straps in order to avoid uncomfortable contact between the chest portion and the wearer's neck and throat.

A resealable pouch may also be disposed along the outside of the chest portion. In some embodiments, the pouch may be sized and configured to enable the device to be compactly self-stowed within the pouch when not in use or being worn by a traveler. It is also contemplated, though, that the pouch may be sized and configured to receive and store various personal belongings, as desired.

Thus, it is an object of the invention to comfortably maintain and support a traveler's arms in line with his or her own body in a manner that avoids conflict with neighboring travelers.

It is another object of the invention to provide means of compactly storing the device when not in use.

It is still another object of the invention to ergonomically maintain and support the traveler's arms while subjected to cramped spaces in public modes of transportation.

One or more of the above-disclosed embodiments, in addition to certain alternatives, are provided in further detail below with reference to the attached figures. The disclosed subject matter is not, however, limited to any particular embodiment disclosed.

Figure 1:
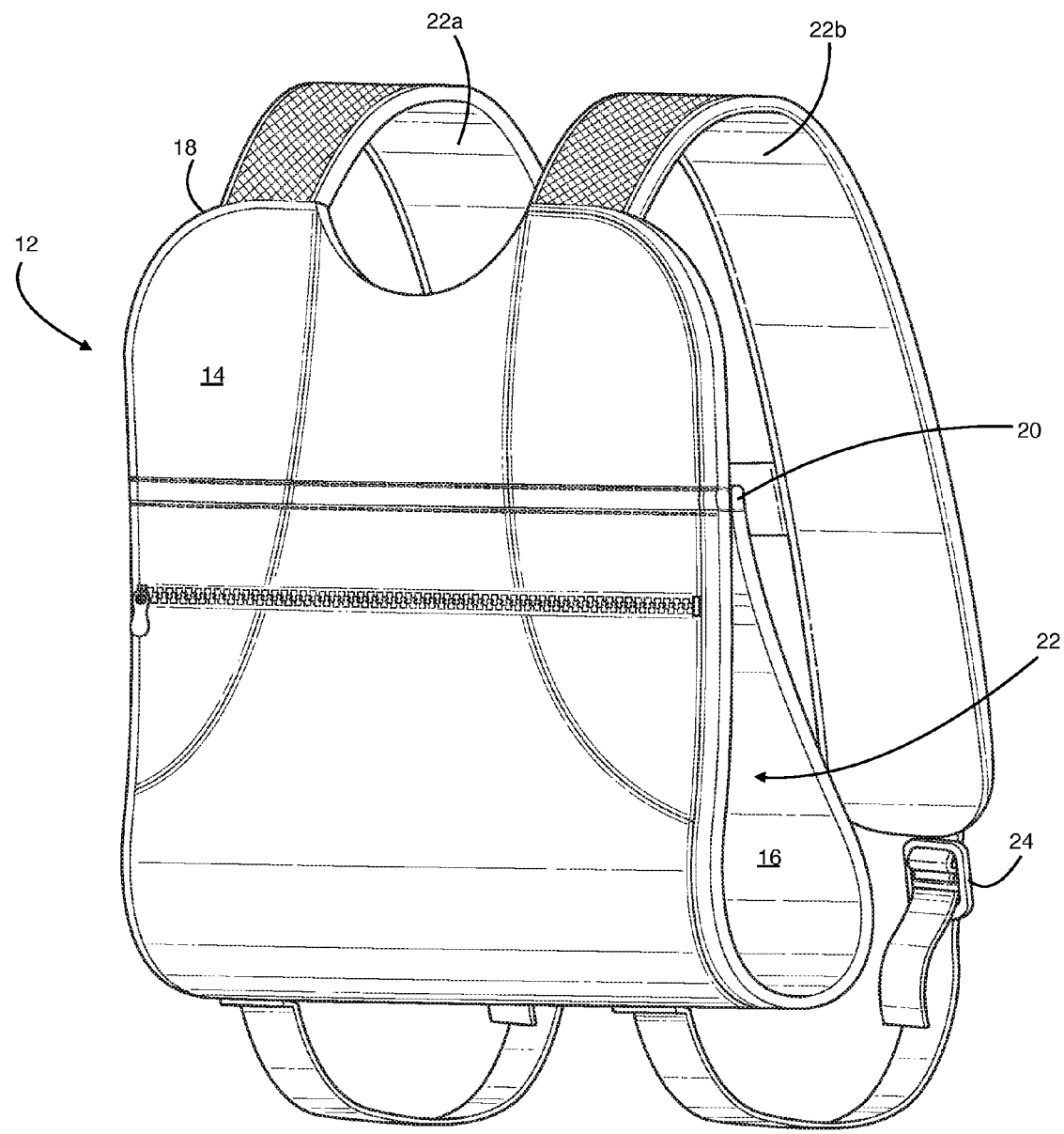
FIG. 1 shows a front perspective view of one embodiment of the travelers' personal arm rest.

The disclosed embodiments may be better understood by referring to the figures in the attached drawings, as provided below. The attached figures are provided as non-limiting examples for providing an enabling description of the method and system claimed. Attention is called to the fact, however, that the appended drawings illustrate only typical embodiments of this invention and are therefore not to be considered as limiting of its scope. One skilled in the art will understand that the invention may be practiced without some of the details included in order to provide a thorough enabling description of such embodiments. Well-known structures and functions have not been shown or described in detail to avoid unnecessarily obscuring the description of the embodiments.

DETAILED DESCRIPTION

Having summarized various aspects of the present disclosure, reference will now be made in detail to that which is illustrated in the drawings. While the disclosure will be described in connection with these drawings, there is no intent to limit it to the embodiment or embodiments disclosed herein. Rather, the intent is to cover all alternatives, modifications and equivalents included within the spirit and scope of the disclosure as defined by the appended claims.

With reference to FIG. 1 the device may comprise a chest portion 12 having an outside 14, an inside 16, a top end 18 and a bottom end 20. A tubular cavity 22 may be formed to receive one or both of a wearer's arms, more particularly his or her forearms, by securing the bottom end 20 along the inside 16 portion of the chest portion 12. In some embodiments, the bottom end 20 may be fixedly secured such as by permanently threadedly stitching the bottom end 20 along the inside 16 of the chest portion 12, such as is shown in the figures. However, it is contemplated that the bottom end 20 may alternatively be adjustably securable along the inside of the chest portion 12. One skilled in the art will recognize, for example and not limitation, that opposing hook and loop fasteners may be respectively secured to the inside 16 of the chest portion 12 and the bottom end 20 so that the bottom end 20 may be releasably and/or adjustably meshed with the inside 16 of the chest portion 12. Similarly, opposing male and female snapping members may be disposed along the inside 16 of the chest portion 12 and the bottom end 20 so that the bottom end 20 may be releasably mated along the inside 16 of the chest portion 12.

Figure 2:
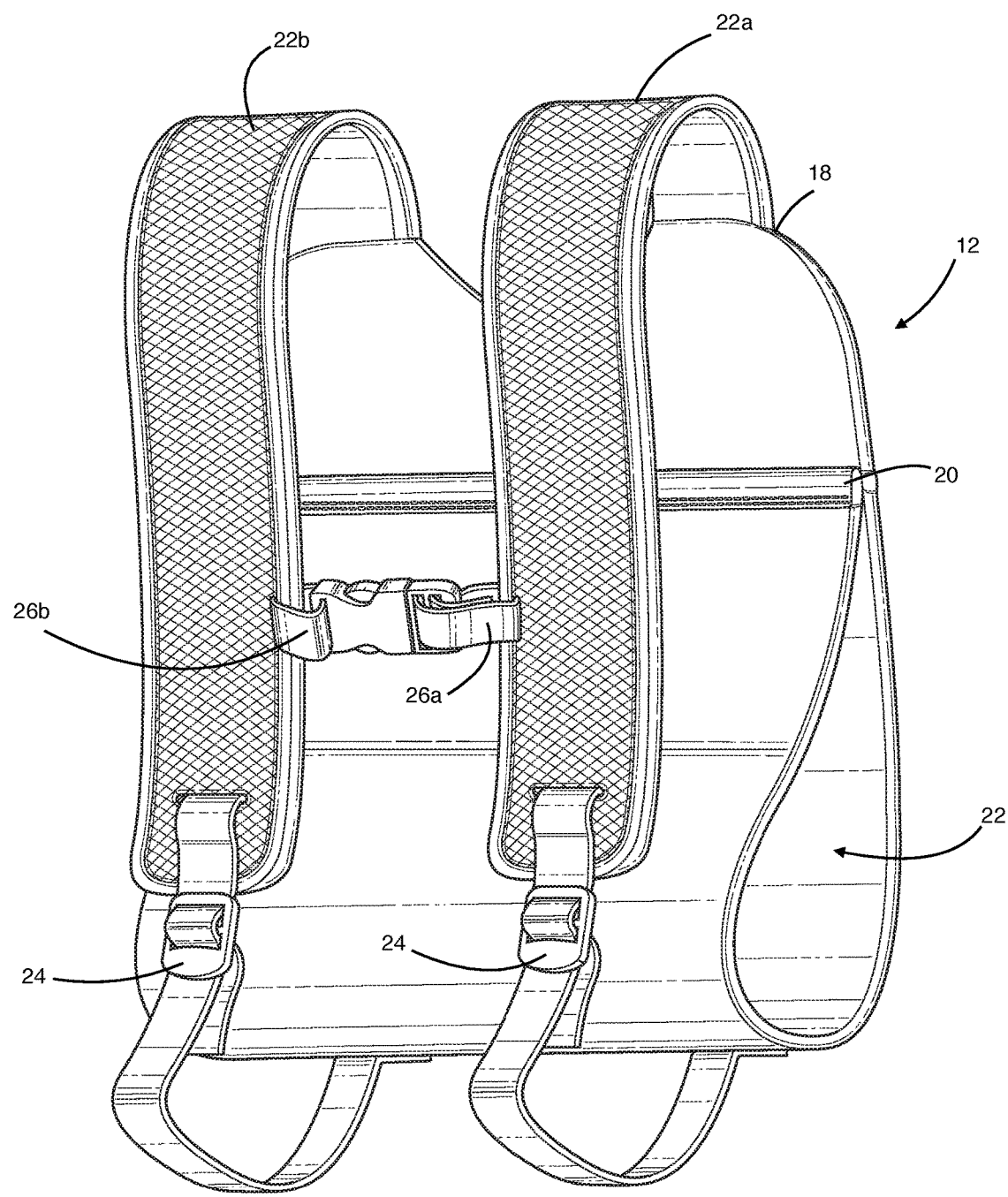
FIG. 2 shows a rear perspective view of one embodiment of the travelers' personal arm rest.
Figure 3:
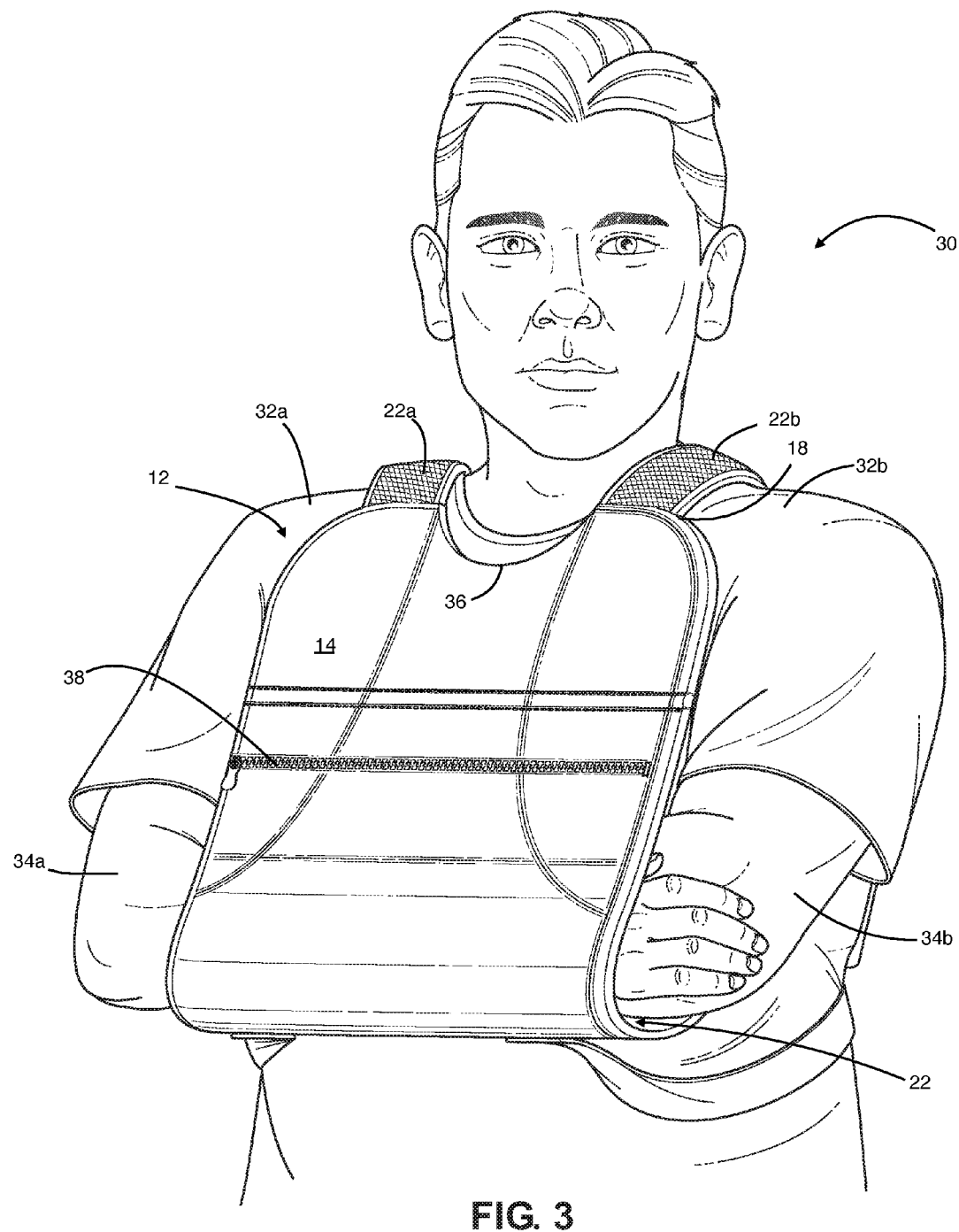
FIG. 3 illustrates one embodiment of the traveler's personal arm rest disposed on a traveler's body.

A first supportive strap 22a and second supportive strap 22b may be secured to the chest portion 12 and configured to comfortably encircle a wearer's 30 left-lateral and right-lateral torso, including his shoulders 32a, 32b as illustrated in FIG. 3. It is contemplated that providing two supportive shoulder straps spreads the weight of a wearer's arms 34a, 34b resting within the tubular cavity 22 evenly across the tops of the wearer's shoulders 32a, 32b. Referring to FIGS. 1 and 2, the first and second supportive straps 22a, 22b may be horizontally spaced from one another and secured to the top end 18 and outside 14 of the chest portion 12 corresponding to a bottom-most portion of the tubular cavity 22. The supportive straps 22a, 22b may thus be configured to receive one each of a wearer's arms therethrough to forcibly hold the chest portion 12 against the wearer's chest.

It is contemplated that the supportive straps 22a, 22b may be adjustable to comfortably fit wearers of various sizes. For example, one skilled in the art will recognize that each supportive strap 22a, 22b may comprise a plastic or metal strap adjuster 24 optionally with locking bars configured to slidably receive portions of the supportive strap 22a, 22b threaded therethrough. Using such adjusters, the lengths of each of the first and second supportive straps 22a, 22b may be increased or decreased as desired.

The chest portion 12 and straps 22a, 22b may comprise a variety of different materials and need not be limited in such respects. It is contemplated that the chest portion may comprise rugged materials capable of withstanding repeated use. Indeed, such materials may also be washable. As a non-limiting example, the chest portion may comprise nylon, vinyl, canvas, polyester, leather, and others, including combinations of any possible materials.

In some embodiments, the chest portion 12 may comprise, in whole or in part, padded material to increase comfort of arms contained therein or even absorb and disperse pressure of contained arms being held against the anterior side of a wearer's torso. Similarly, each of the supportive straps 22a, 22b may comprise padded portions which disperse and absorb pressure applied downward on a wearer's shoulders by crossed arms. Padding in either or both cases may comprise, for example, foam chosen from open cell foam, closed cell foam, dual-density foams, compression molded foams, and even a combination of the same, without limitation. Still, it is contemplated that the traveler's personal arm rest device need only be configured to support the weight of a wearer's arms and any personal belongings stored within a pouch formed therein, thus, one skilled in the art will recognize that it may be desirable to decrease bulk and weight of the device itself by eliminating foamed padding and other similar features altogether.

Other elements may be provided in lieu of or in combination with various forms of padding to ergonomically distribute weight of relaxed, resting arms on the wearer's body. For instance, as illustrated in FIG. 2, a first and second horizontal strap 26a, 26b may be provided to releasably and optionally adjustably connect the first and second shoulder straps 22a, 22b to one another across the thoracic portion of the wearer's back in order to mitigate any tendency for crossed arms to pull the wearer's shoulders forward into an undesirable slumped or slouched position. This may also prevent the first and second supportive straps 22a, 22b from slipping off the wearer's shoulders during use. It is contemplated that such horizontal straps 26a, 26b may be adjustable along the length of the supportive straps 22a, 22b and also adjustable in terms of their own length to accommodate wearers of varied height and girth. Though the horizontal straps 26a, 26b are shown to be connected to one another via a common spring clip 28, one skilled in the art will recognize that the horizontal straps 26a, 26b may be optionally secured to one another via snaps, eye and hook fasteners, hook and loop fasteners, and even simply by tying them together. Thus, ergonomic elements should not be limited by the drawings, which are presented simply to ease understanding.

With reference to FIG. 3, another ergonomic element in the traveler's personal arm rest device may be a concave space 36 between the first and second supportive straps 22a, 22b which defines the shape of the top edge 18 of the chest portion 12. Forming the chest portion 12 in this manner may avoid uncomfortable contact between the chest portion and the wearer's neck and throat.

It is contemplated that a resealable pouch 38 may also be disposed along the outside 14 of the chest portion 12 in some embodiments. More particularly, the pouch 38 may be sized and configured to enable the device to be compactly self-stowed within the pouch 38 when not in use or being worn by a traveler 30. It is also contemplated, though, that the pouch 38 may be sized and configured to receive and store various personal belongings, as desired.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

CONCLUSIONS, RAMIFICATIONS, AND SCOPE

While certain embodiments of the invention have been illustrated and described, various modifications are contemplated and can be made without departing from the spirit and scope of the invention. For example, color applied to various elements comprising the traveler's personal arm rest device may vary according to various aesthetic desires. Additionally, hardware applied to portions of the device may comprise various materials such as plastics, metals, and combinations of the same. Accordingly, it is intended that the invention not be limited, except as by the appended claim(s).

The teachings disclosed herein may be applied to other systems, and may not necessarily be limited to any described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions and concepts of the various references described above to provide yet further embodiments of the invention.

Particular terminology used when describing certain features or aspects of the invention should not be taken to imply that the terminology is being refined herein to be restricted to any specific characteristics, features, or aspects of the traveler's personal arm rest device with which that terminology is associated. In general, the terms used in the following claims should not be constructed to limit the traveler's personal arm rest device to the specific embodiments disclosed in the specification unless the above description section explicitly define such terms. Accordingly, the actual scope encompasses not only the disclosed embodiments, but also all equivalent ways of practicing or implementing the disclosed apparatus. The above description of embodiments of the traveler's personal arm rest device is not intended to be exhaustive or limited to the precise form disclosed above or to a particular field of usage.

While specific embodiments of, and examples for the apparatus are described above for illustrative purposes, various equivalent modifications are possible for which those skilled in the relevant art will recognize.

While certain aspects of the traveler's personal arm rest device disclosed are presented below in particular claim forms, various aspects of the invention are contemplated in any number of claim forms. Thus, the inventor reserves the right to add additional claims after filing the application to pursue such additional claim forms for other aspects of the traveler's personal arm rest device.

What is claimed is:
1. A device for supporting a person's arms in front of his or her body, comprising:

a chest portion having an outside, an inside, a top end, a bottom end, the bottom end securable along the inside to define a tubular cavity sized to receive a wearer's arms;

a first and a second supportive strap, the straps horizontally spaced apart from one another and each of the first and second supportive straps having a first end securable to the top end of the chest portion and a second end securable to a bottom-most portion of the tubular cavity along the outside of the chest portion, the straps further configured to receive one each of a wearer's arms therethrough to respectively encircle at least a portion of the left-lateral and right-lateral of a wearer's torso including his or her shoulder; and a first horizontal strap secured to the first supportive strap and a second horizontal strap secured to the second supportive strap, the first and second horizontal straps releaseably securable to one another.

2. The device of claim 1, wherein the top end defines a concave portion and the first and second supportive straps are secured such that the concave portion defines a horizontal space between the straps.

3. The device of claim 1, further comprising a pouch disposed on the outside of the chest portion.

4. The device of claim 3, wherein the pouch is sized to enable self-stowing of the device when the device is not being worn by a wearer.

5. A device for supporting a person's arms in front of his or her own body during travel comprising:

a chest portion having an outside, an inside, a contoured top end and a bottom end, the bottom end secured along the inside to define a tubular cavity sized to receive a wearer's arms;

a first and a second adjustable supportive strap, the supportive straps horizontally spaced apart from one another and each having a first end fixedly secured to the contoured top end of the chest portion and a second end fixedly secured to a bottom-most portion of the tubular cavity along the outside of the chest portion;

a first horizontal strap secured to the first supportive strap and a second horizontal strap secured to the second supportive strap, the first and second horizontal straps releaseably securable to one another; and a resealable pouch disposed along the outside of the chest portion;

wherein the first and second supportive straps are further configured to receive one each of a wearer's arms therethrough to respectively encircle at least a portion of the left-lateral and right-lateral portions of a wearer's torso including his or her shoulders;

wherein a position of the first and second horizontal straps is adjustable along the first and second supportive straps; and wherein a length of the first and second horizontal straps is adjustable.

6. The device of claim 5, wherein at least a portion of the first and second supportive straps comprises padded material.

7. The device of claim 5, wherein at least a portion of the chest portion comprises padded material.

* * * * *